United States Patent [19]

Ritsky et al.

[11] Patent Number: 5,474,541
[45] Date of Patent: Dec. 12, 1995

[54] VALVED NOZZLE FOR RE-USABLE RESERVOIR OF A FLOWABLE PRODUCT

[75] Inventors: Anthony F. Ritsky; John E. Cameron; Tjalke K. Schuurmans; Russell L. M. Soobrian; Henryk Klakurka; Robert K. Watson; Christopher G. Szumilas, all of Ontario, Canada

[73] Assignee: Astra Pharma, Inc., Mississauga, Canada

[21] Appl. No.: 115,396

[22] Filed: Aug. 31, 1993

Related U.S. Application Data

[63] Continuation of Ser. No. 819,463, Jan. 10, 1992, abandoned.

[51] Int. Cl.$^6$ .................................................. A61M 5/178
[52] U.S. Cl. .................... 604/213; 604/247; 137/533.11; 137/533.15; 222/571
[58] Field of Search .......................... 604/110, 185–186, 604/212–213, 215–216, 245–247, 257, 275, 283, 295, 298, 256, 249; 239/570–571; 137/519, 519.5, 533.17, 533.11, 533, 533.15; 128/912, 200.22; 222/422, 571

[56] References Cited

U.S. PATENT DOCUMENTS

| | | | |
|---|---|---|---|
| 289,528 | 12/1883 | Goodner | 239/327 |
| 342,478 | 5/1886 | Tatum | 137/533.11 |
| 1,576,128 | 3/1926 | Ballard . | |
| 1,725,235 | 8/1929 | Wellensick | 137/519.5 |
| 1,873,782 | 8/1932 | Nixon | 137/533.17 |
| 1,882,314 | 10/1932 | Burt | 137/519.5 |
| 1,903,681 | 4/1933 | Merliss | 604/213 |
| 1,959,043 | 5/1934 | Todd | 137/519 |
| 2,185,173 | 1/1940 | Fortune | 137/519 |
| 2,247,568 | 7/1941 | Armbrust | 137/519 |
| 2,328,014 | 8/1943 | Heigis | 137/519.5 |
| 2,752,199 | 6/1956 | Newell | 239/571 |
| 2,829,719 | 4/1958 | Clark, Jr. | 137/519.5 |
| 3,021,841 | 2/1962 | Burke | 604/213 |
| 3,036,782 | 5/1962 | Windsor | 239/570 |
| 3,356,104 | 12/1967 | Canalizo | 137/519 |
| 3,493,179 | 2/1970 | Lee | 239/327 |
| 3,830,252 | 8/1974 | Follet | 137/519.5 |
| 3,955,648 | 5/1976 | Walker, Jr. et al. | 137/533.11 |
| 3,990,472 | 11/1976 | Etes | 604/247 |
| 4,005,710 | 2/1977 | Zeddies . | |
| 4,059,124 | 11/1977 | Hill | 137/519 |
| 4,197,875 | 4/1980 | Schieferstein et al. | 137/533.11 |
| 4,200,097 | 4/1980 | Hobbs . | |
| 4,286,622 | 9/1981 | Ninomiya et al. | 137/533.11 |
| 4,351,336 | 9/1982 | Sneider . | |
| 4,354,492 | 10/1982 | McPhee | 604/247 |
| 4,474,209 | 10/1984 | Akhtarekhavari . | |
| 4,519,794 | 4/1985 | Sneider . | |
| 4,760,957 | 8/1988 | Rosenberg | 239/570 |
| 4,850,393 | 7/1989 | Lashomb . | |
| 4,945,947 | 8/1990 | Westra et al. | 37/519.5 |
| 4,950,254 | 8/1990 | Andersen . | |
| 5,057,077 | 10/1991 | Turner et al. | 604/247 |

FOREIGN PATENT DOCUMENTS 0459347  1/1937  United Kingdom .................. 604/215

*Primary Examiner*—John D. Yasko
*Assistant Examiner*—Mark Bockelman
*Attorney, Agent, or Firm*—Cohn, Powell & Hind

[57] ABSTRACT

A re-usable nozzle for dispensing a flowable product from a resilient container has a removable one-way valve which facilitates cleaning and sterilisation of the nozzle. When the nozzle is used for dispensing a flowable pharmaceutical, the nozzle controls the amount of suck back of pharmaceutical into the nozzle on completion of dispensing. With a stand off of the valve float from the valve seat during dispensing of about one eighth of an inch (1) the suck back is sufficient to draw any drop of contaminated pharmaceutical at the tip of nozzle on completion of dispensing into the nozzle so as to reduce the risk of contamination of the environment and (2) the suck back is sufficiently small to minimize the risk of damage to any tissue with which the nozzle is intimately associated. Furthermore, with the distance from the valve seat to the nozzle tip being at least about three times the stand off, no contaminated pharmaceutical may enter the container so that the container may be re-used.

5 Claims, 4 Drawing Sheets

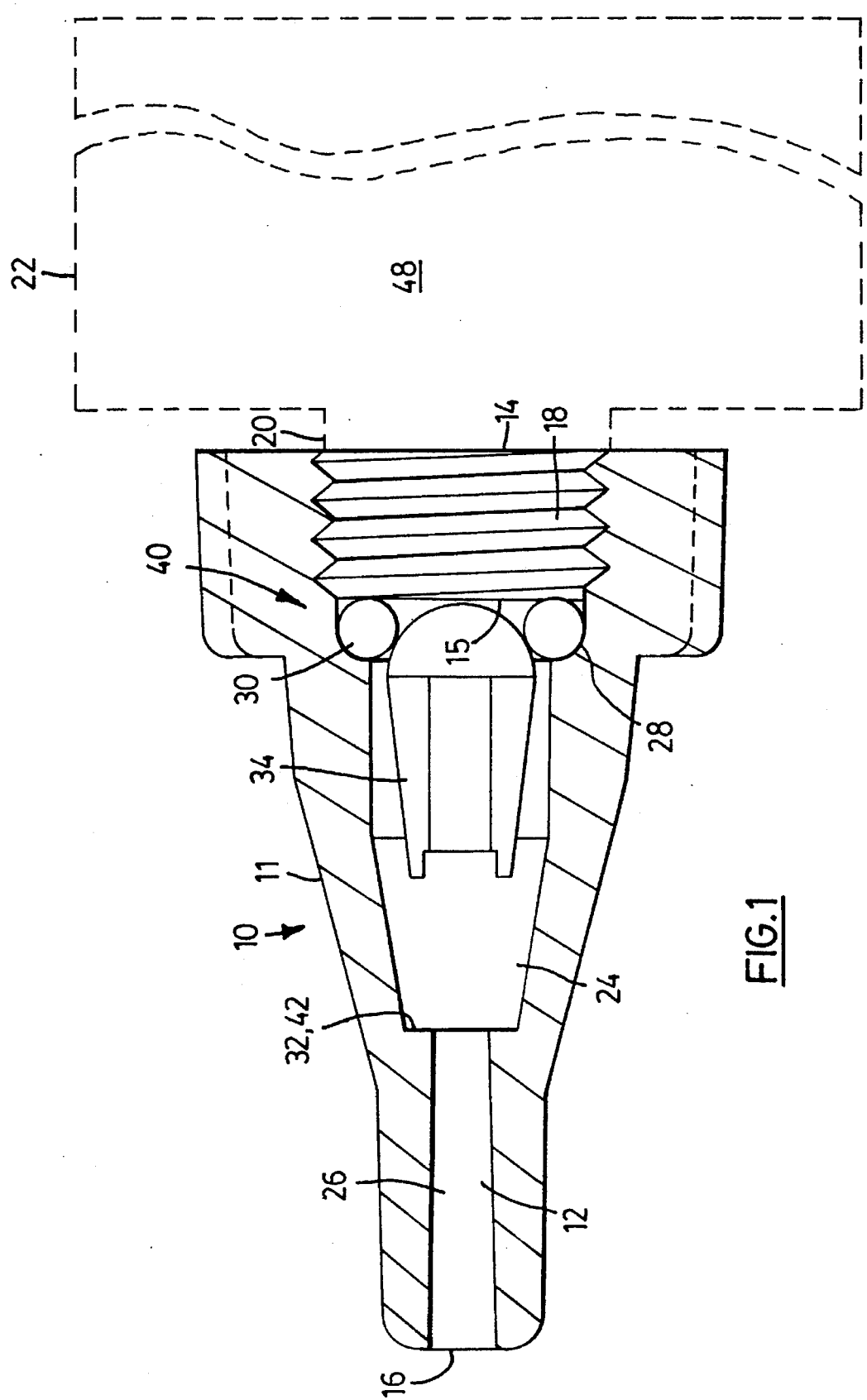

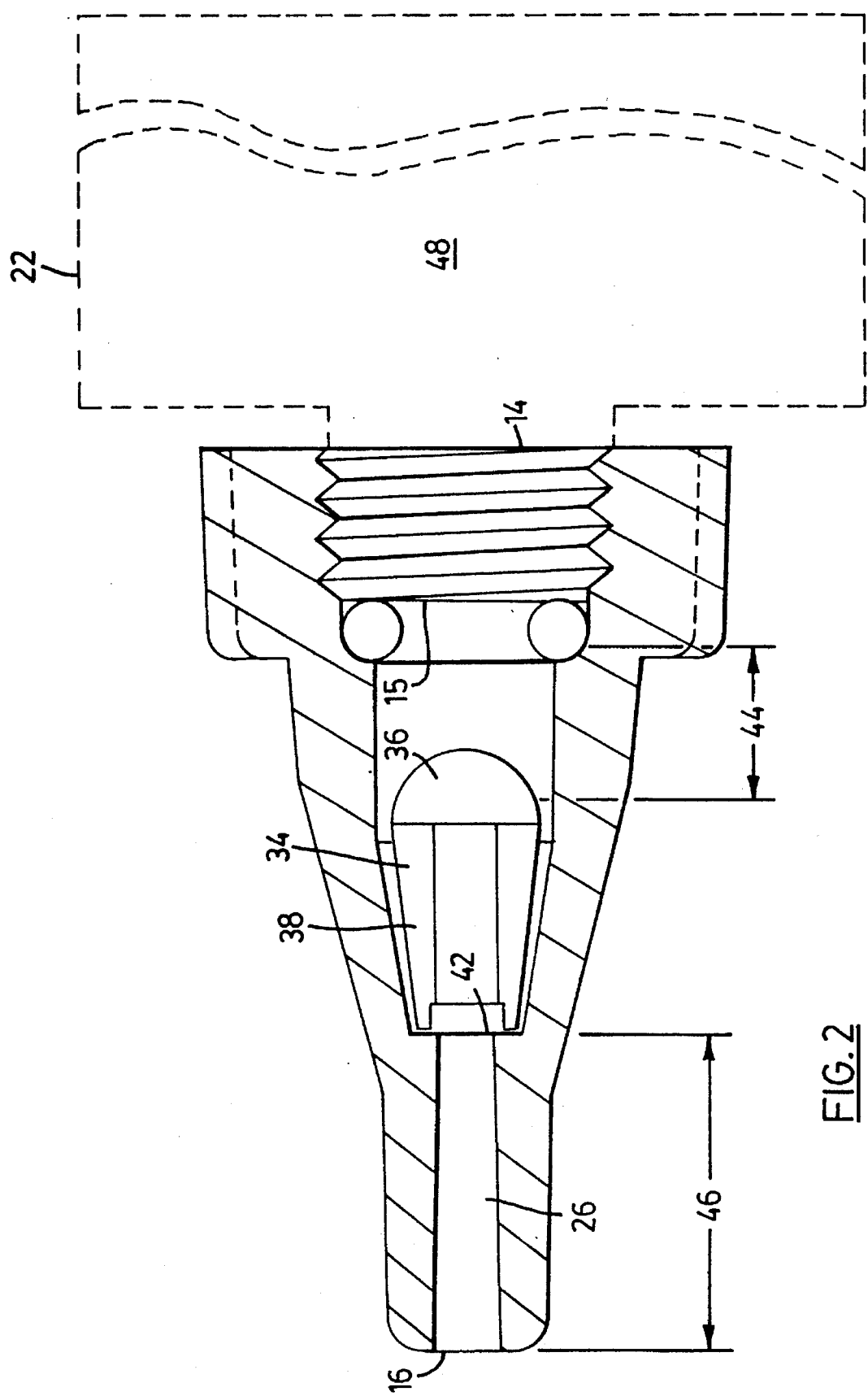

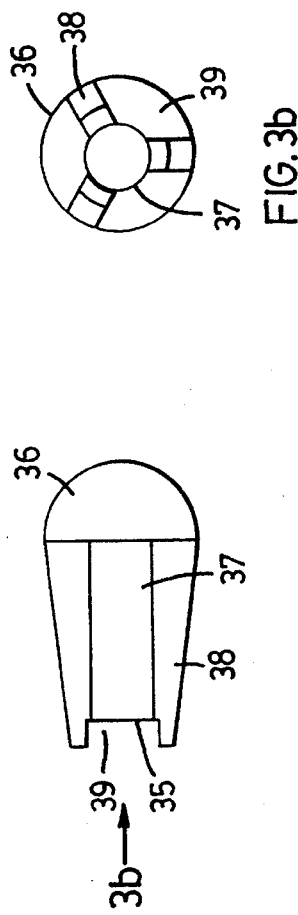
FIG.3a
FIG.3b
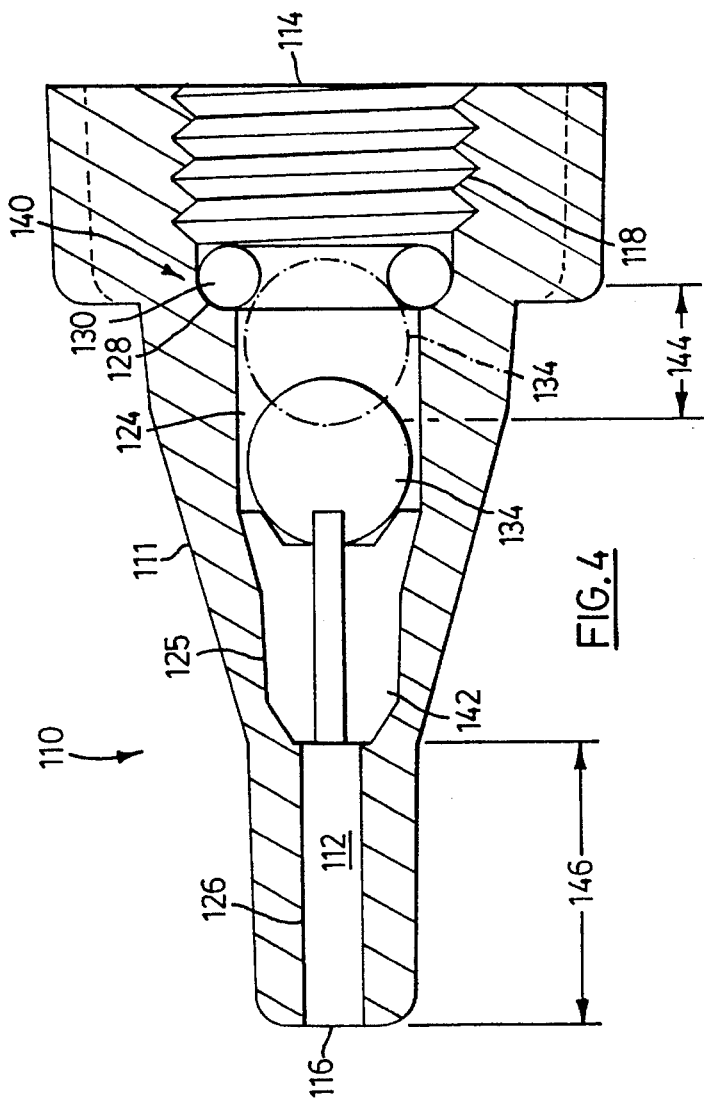
FIG.4

VALVED NOZZLE FOR RE-USABLE RESERVOIR OF A FLOWABLE PRODUCT

This is a continuation of application Ser. No. 07/819,463 filed on Jan. 10, 1992 now abandoned.

BACKGROUND OF THE INVENTION

1. Field of the Invention

This invention relates to a nozzle having a control valve for use with a re-usable reservoir of a flowable product.

2. Description of the Related Art

A flowable pharmaceutical, for example a pharmaceutical jelly, may be stored in a capped collapsible container, typically a capped aluminium tube. When it is desired to dispense some of the pharmaceutical, the cap is removed and typically replaced by a nozzle which provides an unimpeded passageway between the tube and the dispensing end of the nozzle. The nozzle is then directed to the position where the pharmaceutical is to be dispensed, such as in a body orifice, and the container squeezed until the desired amount of pharmaceutical is dispensed. A problem with this equipment is that if the nozzle is placed within a body orifice during a medical procedure, contaminated pharmaceutical may drip from the dispensing end of the nozzle after the nozzle is removed from the orifice. After use, the nozzle is removed, cleaned and then sterilised and the container recapped whereupon the nozzle and container are ready for re-use. However, a further problem with this equipment is that the flowable pharmaceutical may degrade the metals used in the collapsible tube thereby limiting the storage life of the pharmaceutical containing tube.

This invention seeks to overcome drawbacks of the known nozzles.

SUMMARY OF THE INVENTION

According to this invention, there is provided a dispensing system for dispensing a flowable pharmaceutical comprising the following: a resilient container containing a flowable pharmaceutical, said container having a discharge port and providing a positive pressure on being squeezed to dispense pharmaceutical through said discharge port and a negative, suck back, pressure when said container is released; a nozzle comprising: an entry end and a dispensing end and a cavity running between said entry end and said dispensing end; said nozzle tapering to a reduced diameter proximate said dispensing end; means for releasable attaching the entry end of said nozzle to the discharge port of said resilient container; a valve seat comprising a resilient O-ring received within an annular receptor in said nozzle cavity such that said O-ring is removable from said nozzle cavity; a float stop within said nozzle cavity positioned between said valve seat and said dispensing end of said nozzle such that the distance between the dispensing end of the nozzle and said float stop is at least about three times said predetermined standoff distance; a float positioned between said valve seat and said stop and moveable between a first position whereat said float seats on said valve seat and closes said nozzle and a second position whereat said float abuts said float stop such that said nozzle is opened and said float is at a predetermined standoff distance from said valve seat, said standoff distance being about one-eighth inch so that the suck back generated on release of said container after dispensing of flowable pharmaceutical therefrom draws flowable pharmaceutical at said dispensing end of said nozzle into said nozzle to reduce dripping and reseats said float in said valve seat without significant damage to any tissue with which said nozzle may be associated, with said three times distance and said stand-off distance co-operating to ensure no contaminated pharmaceutical enters said container, said float sized such that if said resilient O-ring is removed from said nozzle cavity, said float is removable from said nozzle cavity thereby facilitating cleaning of the nozzle so that the nozzle, once cleaned, may be reassembled and sterilised for reuse, whereby when said nozzle is attached to the discharge port of said resilient container and said container is squeezed, the pressure generated in said nozzle causes said float to lift off said valve seat and abut said float stop so that flowable pharmaceutical in said container may be discharged through the discharge end of said nozzle and whereby, when said resilient container is released, the negative pressure in said nozzle sucks flowable pharmaceutical at said dispensing end of said container into said nozzle and said float into seating relation with said valve seat to close said nozzle, the predetermined standoff distance of said float from said valve seat and said three times distance ensuring no contaminated pharmaceutical re-enters said container while reducing dripping from said nozzle and minimizing damage to any tissue with which said nozzle may be associated.

BRIEF DESCRIPTION OF THE DRAWINGS

In the figures which disclose example embodiments of the invention,

FIG. 1 is a side sectional view of a nozzle made in accordance with this invention attached to a container, FIG. 2 is a side sectional view of the nozzle and container of FIG. 1 showing the nozzle in an open position, FIG. 3 is a side and end view of a portion of FIGS. 1 and 2, FIG. 4 is a side view of another embodiment of this invention.

DESCRIPTION OF THE PREFERRED EMBODIMENTS

Figure 5C:
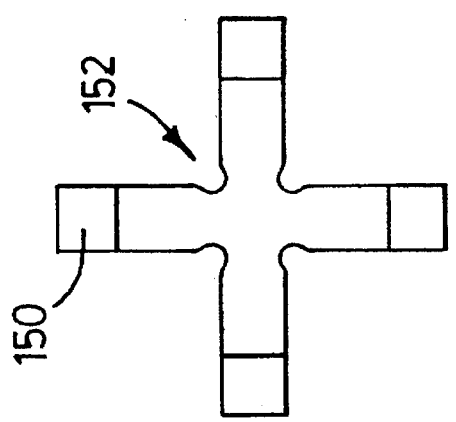
FIG. 5 is a series of views of a portion of FIG. 4.

With reference to FIG. 1, a nozzle 10 has a housing 11 and an interior cavity 12 running between an entry end 14 and a dispensing end 16. The interior cavity has a threaded portion 18 running from the entry end; this threaded portion serves as a means for attachment to the threaded discharge port 20 of a dispensing container 22, shown in phantom in FIG. 1. The interior cavity also comprises an enlarged medial portion 24 and a reduced diameter portion 26 running between the enlarged medial portion 24 and the dispensing end 16 of the nozzle. An annular receptor 28 between the threaded portion 18 and the enlarged medial portion 24 of the interior cavity 12 receives a resilient O-ring 30. The O-ring, when received within the receptor, acts as a valve seat 40 as will become apparent hereinafter. It should be noted that the receptor 28 opens to the entry end 14 of the nozzle which permits removable of the O-ring 30. It may also be noted that the threaded discharge port of the dispensing container is normally screwed into the threaded portion of the nozzle 10 until the end 15 of the discharge port 20 contacts the O-ring 30.

The juncture between the enlarged medial portion 24 of the interior cavity 12 and the reduced diameter portion 26 comprises an annular step 32 which acts as a float stop 42, as will become apparent hereinafter.

A float 34 is received within the interior cavity between the valve seat 40 and the float stop 42. With reference to FIG. 3 as well as FIG. 1, the float comprises a hemispherical end 36, with the hemispherical face directed toward the valve seat and a plurality of legs 38 arranged about a core 37 and depending from the hemispherical end and directed toward the float stop. Flutes 39 are formed between adjacent legs. The legs 38 project beyond the end 35 of the core 37.

The float may be moved between a position whereat the hemispherical end 36 seats on the valve seat, as shown in FIG. 1 and a position whereat the ends of the legs of the float abut the float stop 42, as illustrated in FIG. 2. When the float is seated in the valve seat 40, the interior cavity 12 of the nozzle is closed off, thus closing the nozzle. When the float abuts the float sop, there is fluid communication between the entry end and dispensing end of the nozzle since fluid may pass around the hemispherical end of the float and along the flutes 39 between the legs 38 of the float into the reduced diameter portion 26 of the nozzle. The medial portion 24 of the interior cavity 12 tapers towards the float stop which ensures the float is centred when it moves toward the float stop so that the legs 38 of the float contact the annular float stop.

When the float abuts the float stop 42, the float is at a fixed standoff 44 from the valve seat 40, thus, the standoff is a measure of the distance the float would need to move to seat on the valve seat. This standoff is chosen to be approximately one-eighth of an inch which ensures no significant damage is done to any tissue with which the nozzle is in intimate contact, as will become more apparent hereinafter. The length of the portion 26 of cavity 12, which is the distance 46 between the float stop 42 and the dispensing end 16 of the nozzle, should be at least about three times the standoff 44 to ensure contaminated pharmaceutical does not enter the container 22, as will become more apparent hereinafter.

As is apparent from FIG. 1, the outside diameter of the nozzle 10 tapers to a reduced diameter proximate the dispensing end 16 of the nozzle.

The dispensing container 22 contains a flowable pharmaceutical 48, such as a pharmaceutical jelly. The container is made of a resilient material, such as a resilient plastic.

In operation, a resilient container 22 may be capped. When it is desired to dispense the flowable pharmaceutical 48 contained therein, the cap may be removed and the threaded dispensing port screwed into the threaded portion 18 of nozzle 10 until the end of the dispensing port snugs up against the O-ring 30 of the nozzle. The nozzle may then be directed to the area requiring an application of the pharmaceutical. This may be a body orifice or the portion of a probe intended to be inserted into a body orifice. The tapered nature of nozzle 10 facilitates accurate direction of the nozzle and adapts the nozzle for entry into a body orifice. Once the nozzle has been directed appropriately, the resilient container may be squeezed. This creates a positive pressure (i.e., a pressure greater than atmospheric pressure) in the nozzle which pushes the float 34 into abutment with the float stop 42. With the float abutting the float stop, pharmaceutical is free to be expelled from the container and through the interior cavity 12 of the nozzle 10 to the dispensing end thereof. Dispensing is terminated by releasing the squeezing pressure from the container 22 whereupon, due to its resilience, the container attempts to return to its original shape. This results in a negative pressure (i.e., a pressure less than atmospheric) in the nozzle 10 which sucks the float 34 toward the container 22 and into seating relationship with the valve seat 40. Once the float seats in the valve seat, the nozzle is closed off. Furthermore, the container will not have returned to its original shape when the nozzle is closed off (since the volume increase of the container 22 during suck back will always be less than the decrease in volume in the container when pharmaceutical has been pushed past the float and expelled from the nozzle), consequently the container will apply a static negative pressure to the float which will retain it in seating relation with the valve seat.

The negative pressure in the nozzle prior to the seating of the float on the valve seat draws pharmaceutical back into the nozzle through the dispensing end 16 thereof. Where the nozzle has been inserted in a body orifice, this returned pharmaceutical is contaminated. However, it is intended that the container 22 be re-used (if a significant quantity of pharmaceutical remains therein), consequently, this contaminated pharmaceutical must not re-enter the container. With the distance 46 between the dispensing end of the nozzle and the float stop chosen as at least three times the stand off 44, no contaminated pharmaceutical can reach the container even where the float is significantly denser than the flowable pharmaceutical.

Where the nozzle is intimately associated with delicate tissue inside a body orifice, suck back in the nozzle risks damage to the tissue. It has been determined that limiting the stand off to about one eighth of an inch or less will minimize the risk of tissue damage (independent of the cross-sectional area of the nozzle opening at the dispensing end of the nozzle).

Since pharmaceutical at the dispensing end of the nozzle is sucked back into the nozzle on termination of dispensing, any drip of pharmaceutical formed at the dispensing end will be drawn back into the nozzle if the float stand off is sufficiently large. It has been found that a stand off of about one eighth of an inch is sufficient to draw a drip of pharmaceutical into the nozzle for pharmaceuticals of typical viscosities. Hence, the suck back will assist in the prevention of the dripping of contaminated pharmaceutical from the nozzle.

In the result, a stand off of about one eighth of an inch will be sufficient to draw a drip at the end of the nozzle into the nozzle while minimizing the risk of tissue damage.

After use of the nozzle-container assembly, the nozzle may be removed from the container and the container re-capped. The nozzle may then be readied for cleaning and sterilisation by pulling the O-ring 30 off the annular retainer 28 and out of the nozzle housing through the threaded section 18 of the interior cavity of the nozzle housing and subsequently removing the float from end 14 of the nozzle housing. Thereafter, the nozzle housing and the separated float and O-ring may be cleaned and the nozzle re-assembled and sterilised. The sterilised nozzle and the re-capped container are then ready for re-use.

Figure 5B:
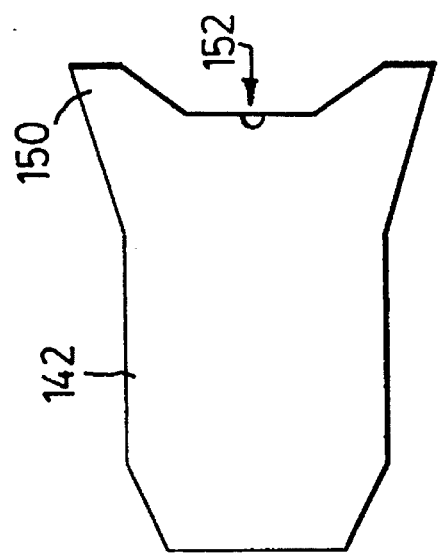
Figure 5A:
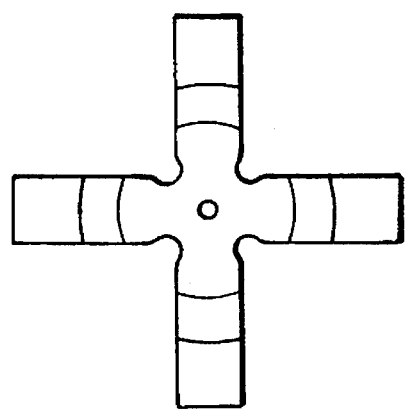

FIGS. 4 and 5 illustrate a second embodiment of the nozzle of this invention. With reference to FIG. 4, a nozzle 110 comprises housing 111 and an interior cavity 112 running between an entry end 114 and a dispensing end 116. The interior cavity has a threaded portion 118 running from the entry end; this threaded portion serves as a means for attachment to the threaded discharge port of a dispensing container, which may be identical to container 22 illustrated in phantom in FIGS. 1 and 2. The interior cavity also comprises an enlarged medial portion 124, a reduced diameter portion 126 running from the dispensing end 116 and a tapered portion 125 running between the enlarged medial portion 124 and the reduced diameter portion 126. An annular receptor 128 between the threaded portion 118 and the enlarged medial portion 124 of the interior cavity 112 receives a resilient O-ring 130. The O-ring, when received within the receptor, acts as a valve seat 140. It should be noted that the receptor 128 opens to the entry end 114 of the nozzle which permits removal of the O-ring 130. It may also be noted that the threaded discharge port of the dispensing container is normally screwed into the threaded portion of the nozzle 110 until the end of the discharge port contacts the O-ring 130.

A float stop 142 is press fit into the tapered section 125 of the interior cavity of the nozzle. The float stop is illustrated in greater detail in FIG. 5. With reference to FIG. 5 it is seen that the float stop is cruciate shaped in cross section and is tapered. The float stop includes fingers 150 about its circumference which form a float receiving area 152. Returning to FIG. 4, it will be apparent that, due to the cruciate shape of the float stop, four channels are formed between the nozzle housing 111 and the float stop when the float stop is press fit into the tapered section of the interior cavity of the nozzle.

A float 134, comprising a spherical ball, is received within the interior cavity between the vale seat 140 and the float stop 142. The float may be moved between a position whereat is seats on the valve seat, as shown in phantom in FIG. 4 and a position whereat it is received between fingers 150 of the float stop and abuts the float stop, as is illustrated in FIG. 4. When the float is seated in the valve seat 140, the interior cavity 112 of the nozzle is closed off, thus closing the nozzle. When the float abuts the float stop, there is fluid communication between the entry end and dispensing end of the nozzle since fluid may pass around the float and along the channels formed between the float stop and the nozzle housing into the reduced diameter portion 126 of the nozzle.

Once again, the stand off 144 is chosen at approximately one-eighth of an inch and the length of the portion 126 of cavity 112, which is the distance 146 between one end of the float stop 142 and the dispensing end 116 of the nozzle, should be at least about three times the standoff 144. Also, nozzle 110 tapers to a reduced diameter proximate its dispensing end 116.

The operation of the nozzle of FIGS. 4 and 5 is the same as the operation of the nozzle of FIGS. 1 through 3, with one exception. To ready the nozzle for cleaning and sterilisation, the float stop 142 is pulled from the nozzle housing after removal of the O-ring and the float. After cleaning of the parts of the nozzle, the float stop is again pressed into the tapered section of the nozzle's interior cavity and the float and O-ring re-assembled so that the nozzle may be sterilised.

Resilient container 22 may be replaced with any other container of the type which may provide a positive pressure to dispense its contents and a suck back pressure on termination of dispensing. Thus, for example, the container could comprise a syringe.

The nozzle of this invention may be used with flowable products other than pharmaceuticals. For example, the nozzle may be used in dispensing an air drying glue. In such an application, the maximum stand off is not critical, however the suck back on termination of dispensing closes the nozzle valve which ensures glue remaining in the container is not exposed to air and hence does not dry while in the container. Furthermore, the ability to disassemble the nozzle allows it to be cleaned for reuse.

Other modifications will be apparent to those skilled in the art and, accordingly, the invention is defined in the claims.

What is claimed is:

1. A dispensing system for dispensing a flowable pharmaceutical comprising the following:

a resilient container containing a flowable pharmaceutical, said container having a discharge port and providing a positive pressure on being squeezed to dispense pharmaceutical through said discharge port and a negative, suck back, pressure when said container is released;

a nozzle attached to said container comprising:
    an entry end and a dispensing end and a cavity running between said entry end and said dispensing end;
    said nozzle tapering to a reduced diameter proximate said dispensing end;
    means for releasably attaching the entry end of said nozzle to the discharge port of said resilient container;
    a valve seat comprising a resilient O-ring received within an annular receptor in said nozzle cavity such that said O-ring is removable from said nozzle cavity when detached from said container;
    a float stop within said nozzle cavity positioned between said valve seat and said dispensing end of said nozzle having a first distance between the float stop and the nozzle dispensing end;
    a float positioned between said valve seat and said float stop and moveable between a first position whereat said float seats on said valve seat and closes said nozzle and a second position whereat said float abuts said float stop such that said nozzle is opened and said float is located at a standoff distance from said valve seat, said standoff distance being about one-eighth inch so that the suck back generated on release of said container after dispensing of flowable pharmaceutical therefrom draws flowable pharmaceutical at said dispensing end of said nozzle into said nozzle to reduce dripping and reseats said float in said valve seat without significant damage to any tissue with which said nozzle may be associated, said first distance being at lest about three times said standoff distance and co-operating such that on release of said container no contaminated pharmaceutical enters said container, said float sized such that if said resilient O-ring is removed from said nozzle cavity, said float is removable from said nozzle cavity thereby facilitating cleaning of the nozzle so that the nozzle, once cleaned, may be reassembled and sterilized for reuse;

whereby when said container is squeezed, the pressure generated in said nozzle causes said float to lift off said valve seat and abut said float stop so that flowable pharmaceutical in said container may be discharged through the dispensing end of said nozzle and whereby, when said resilient container is released, the negative pressure in said nozzle sucks flowable pharmaceutical at said dispensing end of said container into said nozzle and said float into seating relation with said valve seat to close said nozzle, the standoff distance of said float from said valve seat and said first distance ensuring no contaminated pharmaceutical re-enters said container while reducing dripping from said nozzle and minimizing damage to any tissue with which said nozzle may be associated.

2. The dispensing system of claim 1 wherein said float stop is a cruciate insert press fit into said nozzle and wherein said float is a sphere such that said float stop is also removable from said nozzle cavity once said O-ring has been removed.

3. The dispensing system of claim 1 wherein said float stop is an annular abutment and said float has (i) a valve seating end directed toward said valve seat and configured so as to be seatable therein, (ii) a float stop abutting end directed toward said float stop and configured so as to be capable of abutting therewith, and (iii) fluted sides extending to said float stop abutting end.

4. The dispensing system of claim 3 wherein said float comprises a hemispherical portion, with the hemispherical face comprising the valve seating end of said float and a plurality of legs depending from said hemispherical portion, the end of said legs forming said float stop abutting end of said float and said flutes being formed between adjacent ones of said legs.

5. The dispensing system of claim 4 wherein said means for releasably attaching the entry end of said nozzle to the discharge port of said resilient container comprises threads within said nozzle.

* * * * *

UNITED STATES PATENT AND TRADEMARK OFFICE
CERTIFICATE OF CORRECTION

PATENT NO. : 5,474,541

DATED : 12 December 1995

INVENTOR(S) : Anthony F. Ritsky et al.

It is certified that error appears in the above-indentified patent and that said Letters Patent is hereby corrected as shown below:

Column 6, line 41, delete "lest" and insert --least--.

Signed and Sealed this

Sixteenth Day of April, 1996

BRUCE LEHMAN

Attest:

Attesting Officer

Commissioner of Patents and Trademarks